United States Patent [19]

Kurtz et al.

[11] Patent Number: 4,570,620

[45] Date of Patent: Feb. 18, 1986

[54] ADJUSTABLE ORTHOPEDIC SHOE FOR A FOOT SPLINT

[75] Inventors: Robert J. Kurtz, New York; Joseph LiCausi, Port Jefferson Station, both of N.Y.

[73] Assignee: BioResearch Inc., Farmingdale, N.Y.

[21] Appl. No.: 579,584

[22] Filed: Feb. 13, 1984

Related U.S. Application Data

[63] Continuation-in-part of Ser. No. 339,058, Jan. 13, 1982, abandoned.

[51] Int. Cl.[4] ............................................. A61F 3/00
[52] U.S. Cl. ................................. 128/80 A; 128/87 C
[58] Field of Search ................... 128/80 A, 88, 87 R, 128/80, 83

[56] References Cited

U.S. PATENT DOCUMENTS

3,892,231  7/1975  Tummillo .................... 128/80 A
4,249,523  2/1981  Bidwell ....................... 128/80 A Primary Examiner—John D. Yasko
Assistant Examiner—C. Scott
Attorney, Agent, or Firm—Larson and Taylor

[57] ABSTRACT

An adjustable orthopedic shoe for a foot splint is disclosed. The shoe is split into a toe portion and a heel portion to which a toe plate and a heel plate are respectively attached. The toe plate is adjustable relative to the heel plate about a longitudinal axis, a lateral axis, an oblique axis, or a combination of axes. After adjustment, the toe plate is locked in position relative to the heel plate by flanges depending from the plates. Preferably, the flanges are rounded and contact the ground and a pair of shoes are provided which are attached to an orthopedic foot splint. The foot splint maintains a desired angle between the feet of the user but otherwise allows virtually full freedom of movement of the feet.

9 Claims, 14 Drawing Figures

ADJUSTABLE ORTHOPEDIC SHOE FOR A FOOT SPLINT

This is a continuation in-part application of Ser. No. 339,058 filed January 13, 1982, now abandoned.

FIELD OF THE INVENTION

This invention relates generally to the field of orthopedic shoes for foot splints and more particularly to such a shoe which allows the toe of the shoe to be adjusted.

BACKGROUND OF THE INVENTION

In general, an orthopedic foot splint is useful in correcting bone deformities, particularly in children, by holding the patient's feet at an appropriate corrective angle. Thus, if a patient's feet are abnormally toed-in, it is recommended that the patient wear a splint for specified period which will hold the feet in a corrective toed-out position. A common type of prior art device, as disclosed in U.S. Pat. Nos. 2,920,620 to Rogers; 4,040,416 to Zentman; and 4,008,129 to Digiulio, includes a pair of shoes mounted on a flat bar. The shoes in these devices are adjustable on the bar to provide a variety of different toe-in and toe-out angles, but are not otherwise adjustable. Unfortunately, these prior art devices are extremely uncomfortable to the patient as they maintain the feet in almost rigid positions. Even the patent to Zentman which includes a flexible spacer bar to allow a slight amount of vertical movement does little to alleviate this problem. In addition, the patient cannot move except by hopping, which is dangerous and perhaps impossible for young children to perform.

To overcome this almost total lack of mobility and extreme discomfort, prior art devices have been proposed which to allow some movement as well. For instance, in U.S. Pat. No. 2,963,020 to Moran, a device is disclosed which comprises a separate member attached to each shoe of the patient which members are connected by parallelogram links. These linkages are pivotally attached to each shoe member and this allows movement of the feet both upwards and downwards, and forwards and rearwards. In addition, the length of the linkages is manually adjustable. U.S. Pat. No. 3,487,829 to Barnett also discloses parallelogram links connecting shoe engaging members. In this device, the parallelogram links are attached to the shoe engaging members by ball and socket joints. This device also allows the feet to move forwards and backwards, and upwards and downwards, as well as as allowing the ends of the shoes to tilt upwards or downwards somewhat.

In U.S. Pat. No. 4,249,523 to Bidwell, an adjustable orthopedic foot splint to which a pair of shoes are attached is disclosed which maintains a desired angle between the shoes but which otherwise allows virtually full freedom of movement of the shoes. While the foot splint disclosed in the patent is a vast improvement over the prior art types of foot splint mentioned above, none of the prior art devices has a shoe in which the forward part of the foot can be urged up or down or urged to rotate relative to the rear part of the foot, especially when the feet are further restrained by a foot splint.

SUMMARY OF THE INVENTION

The present invention provides a novel shoe for urging the toe and heel parts of a patient's foot to a desired position to treat various problems including forefoot aductions, hind foot inversions, and hind for equinus. The present invention also provides a means for selecting a variety of different positions at which the parts of the patient's foot are maintained.

According to the present invention an orthopedic shoe is separated into a heel portion and a toe portion to which a heel plate and a toe plate are respectively attached. The toe plate is adjustable relative to the heel plate about a longitudinal axis, about a lateral axis, about an oblique axis or about a combination of axes. The toe plate is then locked in place at the position desired so that the toe part of the foot of the user can be urged relative to the heel part as desired. Flanges depending from the bottom of the plates are provided to lock the toe plate relative to the heel plate at one of a plurality of different positions. The flanges are rounded and may contact the ground.

An object of the invention is to provide shoes which maintain the parts of the patient's foot at a desired position while the shoes are attached to a foot splint which provides the feet with almost full mobility otherwise. Thus, the patient can walk, climb stairs, or crawl in an approximately normal manner.

It is a further object of the invention to provide a more comfortable apparatus for holding the parts of a foot at a desired position while the feet are at a desired angle. With the exception of the angle between the patient's feet, the foot splint allows the patient to move his feet to almost any position which he finds comfortable. In addition, the discomfort of not being relatively ambulatory is also eliminated.

Other features, objects and advantages of the present invention are stated in or apparent from the detailed description of the presently preferred embodiments of the invention found hereinbelow.

DETAILED DESCRIPTION OF THE PREFERRED EMBODIMENTS

Figure 1:
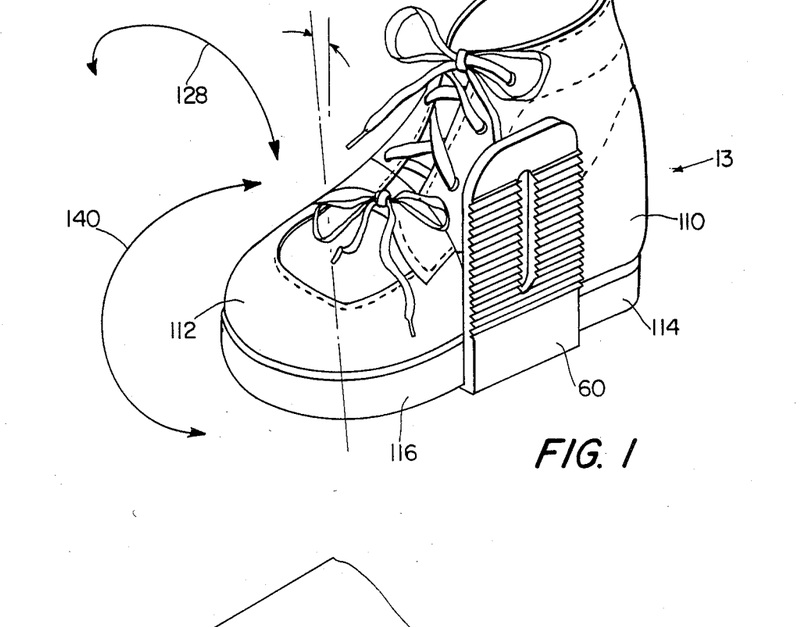
FIG. 1 is a perspective view of an orthopedic shoe of the present invention.
Figure 2:
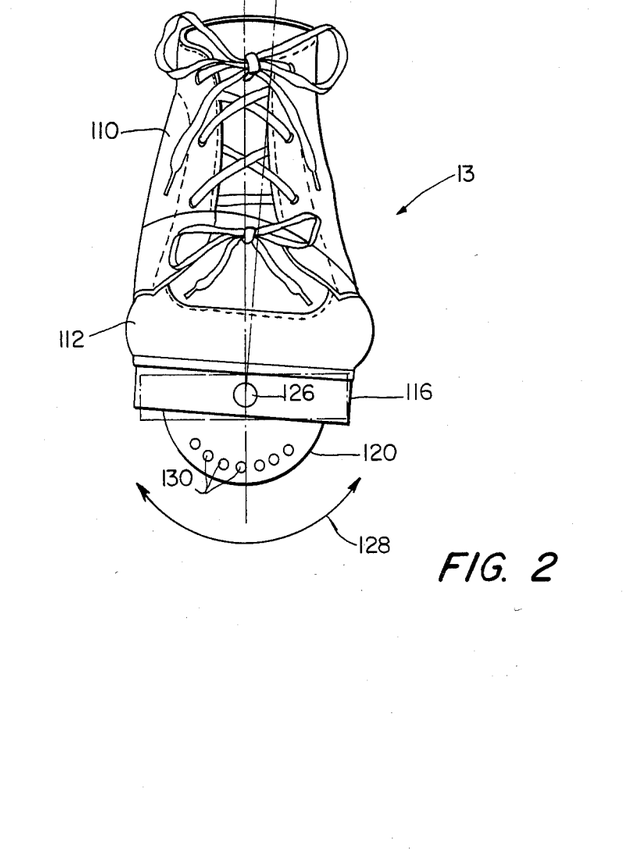
FIG. 2 is a front view of the shoe depicted in FIG. 1.
Figure 3:
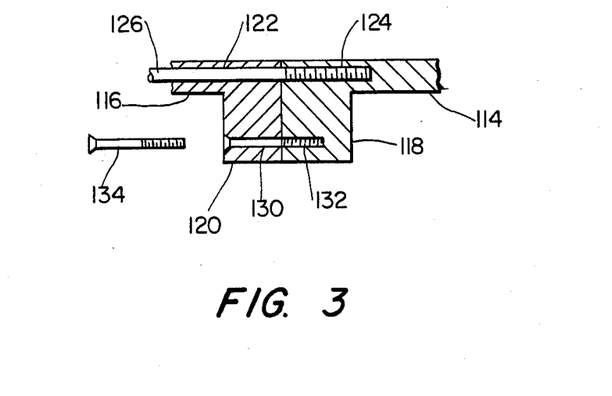
FIG. 3 is a cross-sectional side view of the adjusting mechanism for the toe of the shoe depicted in FIG. 2.

With reference now to the drawings in which like numerals represent like elements throughout the several views, a presently preferred embodiment of the present invention is depicted in FIGS. 1 to 3 and includes a shoe 13 which the patient wears when using an orthopedic foot splint to be described subsequently. Shoe 13, which defines a longitudinal axis, is separated into two portions, a heel portion 110 and a toe portion 112. Toe portion 112 is telescopically received in heel portion 110 for a short distance. Attached to the bottoms of heel portion 110 and toe portion 112 are, respectively, a heel plate 114 and a toe plate 116. Upstanding from one side of heel plate 114 is an upstanding plate 60.

As shown best in FIGS. 2 and 3, depending from the bottoms of heel plate 114 and toe plate 116 at the adjacent lateral edges thereof are, respectively, a heel flange 118 and a toe flange 120. Both heel flange 118 and toe flange 120 are rounded on the bottm and are integrally formed with respective plates 114 and 116. Toe plate 116 has a longitudinal bore 122 therethrough which aligns with a longitudinal bore 124 in heel plate 114. Toe plate 116 is rotatably mounted to heel plate 114 by a threaded bolt 126 passing through bore 122 of toe plate 116 and engaged in threaded bore 124 of heel plate 114. This allows toe plate 116 and toe portion 112 to rotate or be adjusted relative to heel plate 114 and heel portion 110 as shown by arrow 128.

Toe flange 120 includes a series of bores 130 therethrough which are arranged in a circle having a center coaxial with the longitudinal axis of bolt 126. Bores 130 are arranged approximately every 5° and preferably there are seven such bores 130. Heel flange 120 includes a single threaded bore 132 which is located so as to align with any one of bores 130. A threaded screw 134 is provided which extends through the bore 130 aligned with threaded bore 132 and engages threaded bore 132. In this manner, toe plate 116, which rotates relative to heel plate 114, can be locked in a desired rotational position by inserting threaded screw 134 in the appropriate bore 130 and engaging threaded bore 132. Obviously, this also causes toe portion 112 to be rotated relative to heel portion 110 and the relative rotational alignment can be easily changed in increments of 5° about the vertical by removing screw 134 and bringing the appropriate bore 130 into alignment with threaded bore 132. Flanges 118 and 120 are then easily locked in place again by screw 134.

Figures 4, 5:
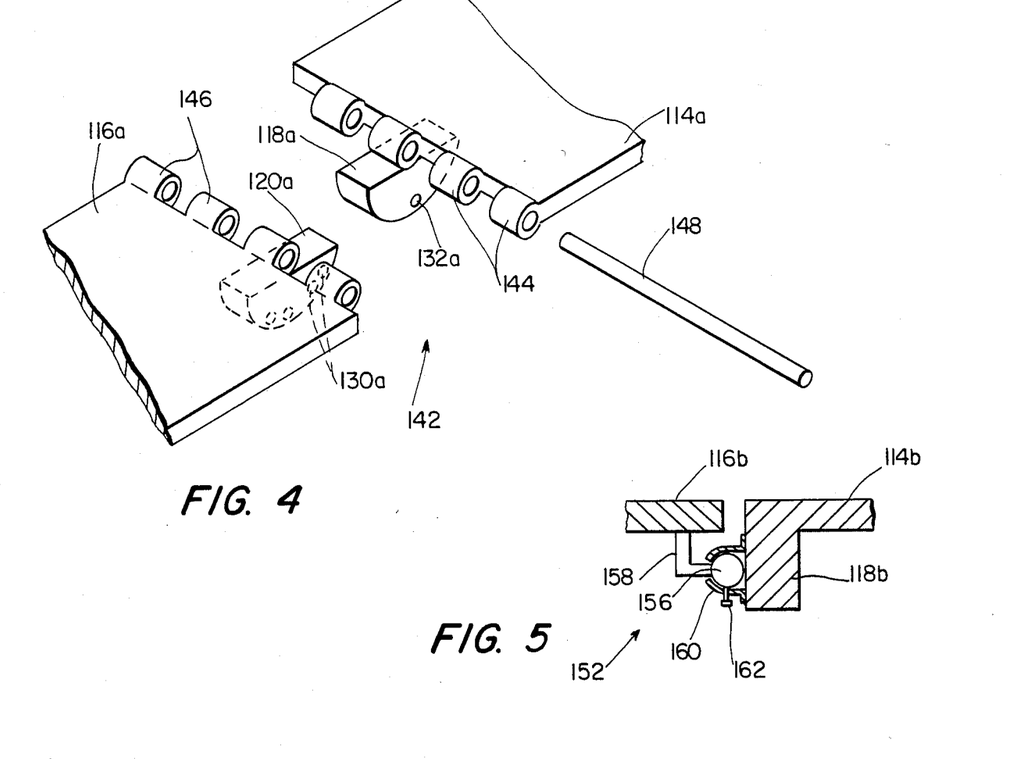
FIG. 4 is a perspective view of an alternative adjusting mechanism of the present invention.
FIG. 5 is a cross-sectional side view of another alternative adjusting mechanism of the present invention.

Besides the adjustment of toe portion 112 relative to heel portion 110 depicted by arrow 128, it is also desirable to allow adjustment of toe portion 112 relative to heel portion 110 as depicted by arrow 140. To accomplish this alternative, adjustment device 142 shown in FIG. 4 is used. Adjusting device 142 includes mating hinge elements 144 and 146 located on the adjacent lateral edges, respectively, of a heel plate 114a and a toe plate 116a. Coupling hinge elements 144 and 146 together is a hinge pin 148. In this manner, heel plate 114a is rotatably mounted about hinge pin 148 to toe plate 116a.

Extending from the bottom of the toe plate 116a and toward heel plate 114a is a toe flange 120a. Toe flange 120a includes a series of bores 130a which are located in circle concentric with the longitudinal axis of hinge pin 148, similar to bores 130 of toe flange 120. When heel plate 14a is attached to toe plate 116a, toe flange 120a is located immediately adjacent a heel flange 118a. Heel flange 118a extends from the bottom of heel plate 114a and towards toe plate 116a. In a manner similar to heel flange 118, heel flange 118a is provided with a threaded bore 132a which aligns with any one of bores 130a of toe flange 120a. Thus, it is possible to rotate toe plate 116a (and the attached toe portion) relative to heel plate 114a (and the attached heel portion) about the lateral axis formed by hinge pin 148 and to subsequently lock toe plate 116a and heel plate 114a in this position by use of a suitable screw.

Depicted in FIG. 5 is another alternate embodiment of an adjustment device 152 which consists of a universal joint 154.

Adjustment device 152 is used to adjust toe plate 116b relative to toe plate 1114b in both directions indicated by arrows 128 and 140. Universal joint 154 includes a ball 156 which is rigidly attached to toe plate 116b by an arm 158. Ball 156 is received in a socket 160 which is securely attached to a heel flange 118b extending down from the lateral edge of heel plate 114b. Three set screws 162 (only one of which is shown) extend through socket 160 to lock ball 156 immovably in socket 160. By use of universal joint 154, row plate 116b (and the attached toe portion) is easily and quickly rotatable about a lateral and/or longitudinal axis relative to heel plate 114b (and the attached heel portion). Once toe plate 116b is positioned as desired, set screws 162 are then used to lock toe plate 116b in place relative to heel plate 114b.

Preferably, shoes 13 are designed to be used in conjunction with an orthopedic foot splint such as disclosed in U.S. Pat. No. 4,249,523, which is herein incorporated by reference. Such a foot splint is depicted in FIGS. 6 to 9A. Briefly, the operative portions of such a foot print include a heel plate pivot means 10, a linkage means 11, and a central pivot means 12. Each patient using the foot splint wears a special pair of fitted shoes 13 described above which include heel plates 14. To provide a pivot means 10, an upstanding plate 15 extends upwards alongs the inside edge of each heel plate 14. A pivot arm 16 is attached to each upstanding plate 15 by means of rivets 18. Each rivet 18 is used to form a pivot axis about which pivot arm 16 pivots. Each pivot arm 16 also includes a vertical slot 20 so that each pivot arm has a means to slide vertically in relation to the pivot axis along the face of upstanding plate 15. In this embodiment, the distal end of each pivot arm 16 forms one leaf of a hinge element 22. Each hinge element 22 has a horizontally extending pivot axis. The other leaf of each hinge element 22 has an inwardly directed right angle turn 24.

Figures 6, 7:
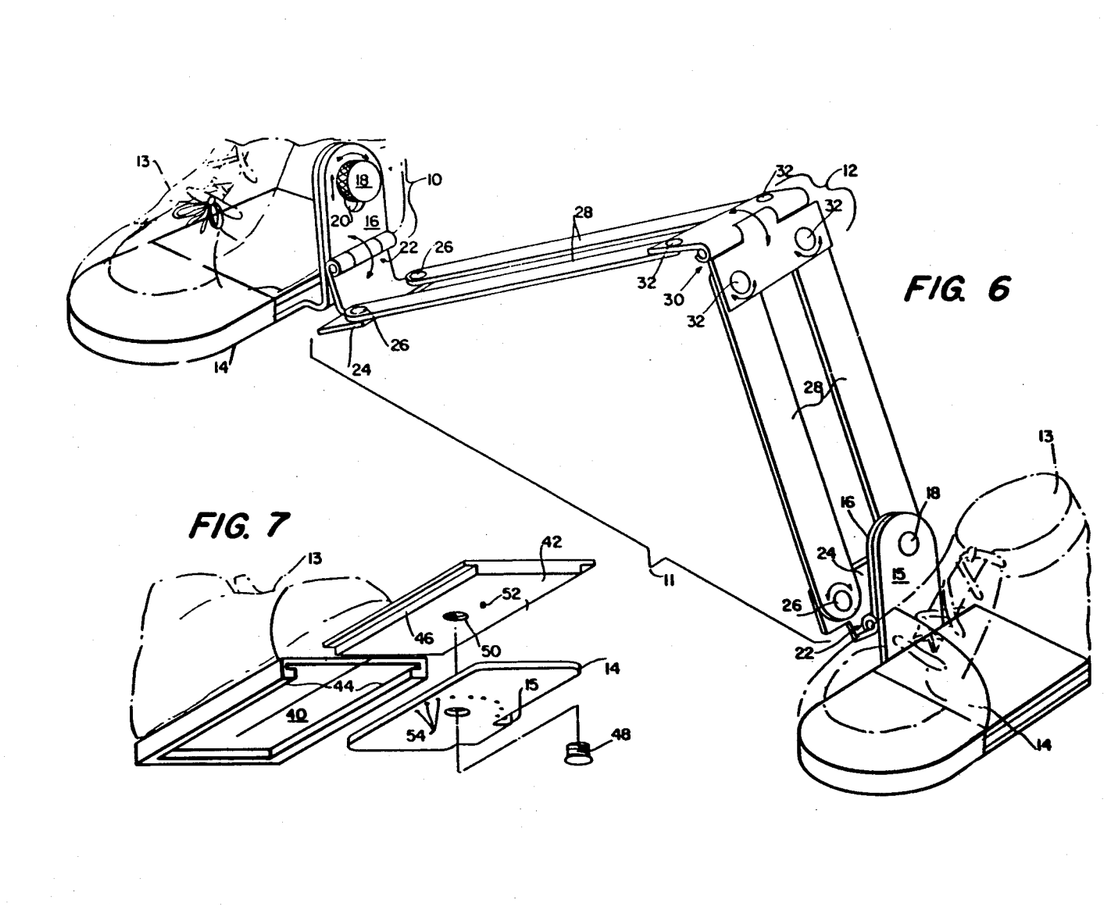
FIG. 6 is a perspective of an embodiment of an orthopedic foot splint.
FIG. 7 is an expanded perspective view of the adjustable shoe engaging means used in one embodiment of the present invention.

Linkage means 11 includes two pairs of parallelogram links 28. Each pair of parallelogram links 28 is pivotally connected to a corresponding right angle turn 24 by rivets 26. Finally, central pivot means 12 includes a central hinge element 30 which interconnects each pair of parallelogram links 28 to form a unitary foot splint. Central hinge element 30 has a horizontally extending axis which is parallel to the axis of hinge element 22. Additionally, each pair of parallelogram links 28 are pivotally attached to a respective leaf of central hinge element 30 by rivets 32 so that each pair of parallelogram links 28 remain parallel at all times when the pairs of parallelogram links 28 pivot.

Referring now to FIG. 7, a means to adjustably attach heel portion 110 of heel plate 14 at a plurality of different angular orientations is shown. The means includes a mounting plate 40 which is rigidly attached to the sole heel portion 110 of shoe 13. Mounting plate 40 is designed to slide onto an angular adjusting plate 42 by means of inturned edges 44 on mounting plate 40 which mate with reduced edges 46 on angular adjusting plate 42. In turn, angular adjusting plate 42 is designed to be attached to heel plate 14 by means of a screw 48 which passes through heel plate 14 to a threaded bore 50 in angular adjusting plate 42. A pin 52, depending from angular adjusting plate 42, is received in one of a plurality of correspondingly spaced receiving holes 54 in heel plate 14. When screw 48 attaches angular adjusting plate 42 to heel plate 14, pin 52 prevents angular adjusting plate 42 from rotating on heel plate 14 about screw 48. The thickness of angular adjusting plate 42 must also be less than the depth from the bottom surface of mounting plate 40 to the bottom surface of inturned edges 44. Thus, as angular plate 42 is pulled down towards heel plate 14 by screw 48, angular plate 42 acts to hold mounting plate 40 frictionally against heel plate 14. Therefore, when screw 48 is snug, heel portion 110 of mounting plate 40, angular adjusting plate 42 and heel plate 14 are all rigidly held together as a unit.

In operation, the foot splint is used in the following manner. After determining the angle at which the patient needs his feet to be kept, screw 48 is loosened enough to permit angular adjusting plate 42 to rotate about screw 48. Pin 52 is then moved to a receiving hole 54 which corresponds to the angle at which the feet are to be kept. Next, screw 48 tightened and the patient puts on shoes 13. The foot splint acts to keep shoes 13 always at the angular orientation which was chosen. However, shoes 13 remain free to move in an otherwise almost normal manner. By way of illustration, the patient's feet can move forward and backwards as parallelogram links 28 pivot on rivets 26 and 32. The patient's feet also move upwards and downwards by reason of hinge elements 22 and central central hing 30. Hinge elements 22 and central hinge 30 also allow the patient's feet to move together and apart. Lastly, the patients's feet can tilt upwards and downwards as well due to the action of plate pivot means 10. Thus the patient can walk or climb steps in an almost normal manner. And if the foot splint is used on an infant, not only can the infant crawl in an almost normal manner, but the infant's efforts towards learning to walk are not unduly impeded. The only movement which is impeded in the toeing-in or toeing-out of the feet.

Figure 8:
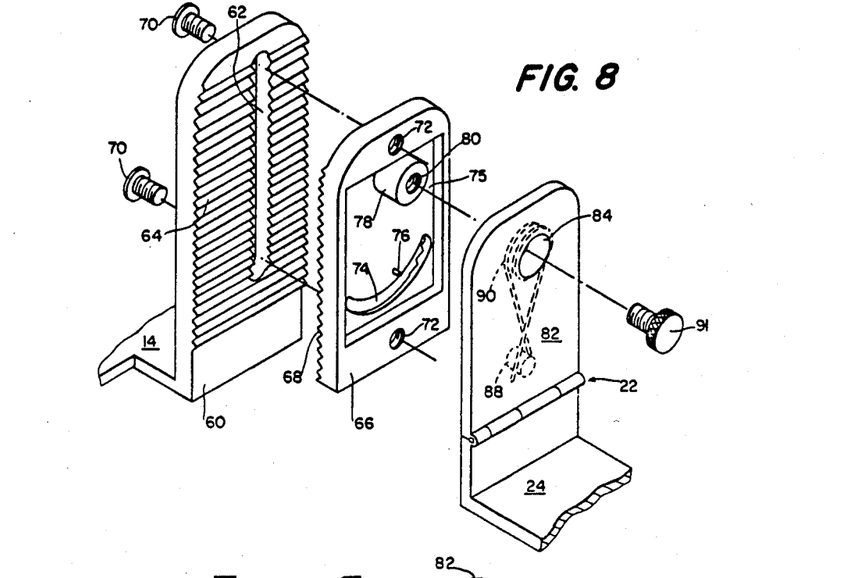
FIG. 8 and 8A are an expanded perspective view and a side view, respectively, showing another embodiment of the orthopedic foot splint with a link positioning means and a restrictive tilting mechanism.
Figure 8A:
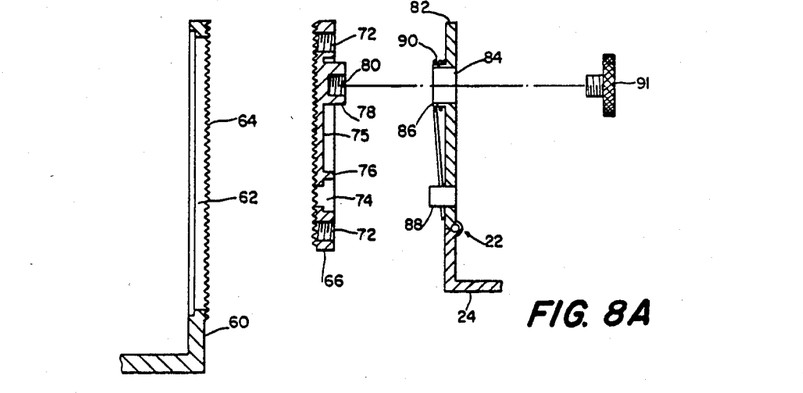

With reference now to FIGS. 8 and 8A, an alternative embodiment of plate pivot means 10 is depicted. In this embodiment, means are provided to raise and lower the pivot axis of pivot arm 82. A means is also provided to limit the angular pivoting of pivot arm 82 and to urge pivot arm 82 to a position perpendicular to heel plate 14. Only a portion of heel plate 14 is shown, and this portion shows upstanding plate 60 attached along the inside edge of heel plate 14. Also depicted are facing plate 66 and pivot arm 82 which includes hinge element 22.

Upstanding platea 60 has a vertical slot 62 therethrough, and the inner face is covered with a series of horizontal grooves forming a serrated face 64. Located opposite serrated face 64 is a matching serrated face 68 on facing plate 66. Facing plate 66 is attached to upstanding plate 60 by screws 70 which pass through vertical slot 62 and engage facing plate 66 in threaded bore 72. Facing plate 66 also has an arcuate keyway 74 therethrough. Located in a recessed portion 75 on the face of facing plate 66 opposite to serrated face 68 are a peg 76 and a pivot post 78 having threaded bore 80. Pivot post 78 extends beyond the face of facing plate 66, a distance which is slightly longer than the thickness of pivot arm 82. Pivot arm 82 has a bore 84 which pivot post 78 extends through slightly. In addition, a pivot sleeve 86 extends outward from the face of pivot arm 82 and extends around pivot post 78. A raised key 88 also extends outward from the face of pivot arm 82. Surrounding pivot sleeve 86 is a spiral spring 90 whose ends are crossed and lie on either side of raised key 88. A screw 91, which passes through bore 84 into threaded bore 80, attaches pivot arm 82 facing plate 66.

In operation, this alternative embodiment of plate pivot means 10 functions in the following manner. Depending on what is most comfortable or preferred by the patient, the position of right angle turn 24 and hence the height of linkage means 11 relative to heel plate 14 can be adjusted. This adjustment is accomplished by attaching facing plate 66 to upstanding plate 60 at a variety of different heights which causes the pivot arm 60 and right angle turn 24 to move as well. To adjust the height of facing plate 66, screws 70 are loosened until there is sufficient clearance between serrated faces 64 and 68 to allow facing plate 66 to slide along upstanding plate 60. It is then a simple matter to select the height of facing plate 66 which the patient prefers and to tighten screws 70. The engagement of matching serrated faces 64 and 68 locks facing plate 66 onto upstanding plate 60 as screws 70 are tightened. Linkage means 11, whose height is determined by facing plate 66, is likewise positioned at the selected height.

The means to limit the angular pivoting of pivot arm 60 and to urge pivot arm 60 to a position perpendicular to heel plate 14 function in the following manner. Screw 91 is used to attach pivot arm 82 to facing plate 66. Screw 91 is not tightened until key 88 extends into arcuate keyway 74 and peg 76 is located between the two crossed ends of spiral spring 90. When screw 91 is tightened down, it engages the end of pivot post 78 so that pivot arm 82 pivots freely about pivot post 78. However, with key 88 in arcuate keyway 74, the pivoting of pivot arm 82 is restricted by the travel of key 88 from one end of arcuate keyway 74 to the other. In addition, as pivot arm 82 moves away from a perpendicular orientation, peg 76 engages a corresponding end of sprial spring 90 while the other end of spiral spring 90 engages key 88. This causes spiral spring 90 to exert force on pivot arm 82, urging it back to a perpendicular orientation where neither end of spiral spring 90 is engaged with peg 76.

Figures 9, 9A:
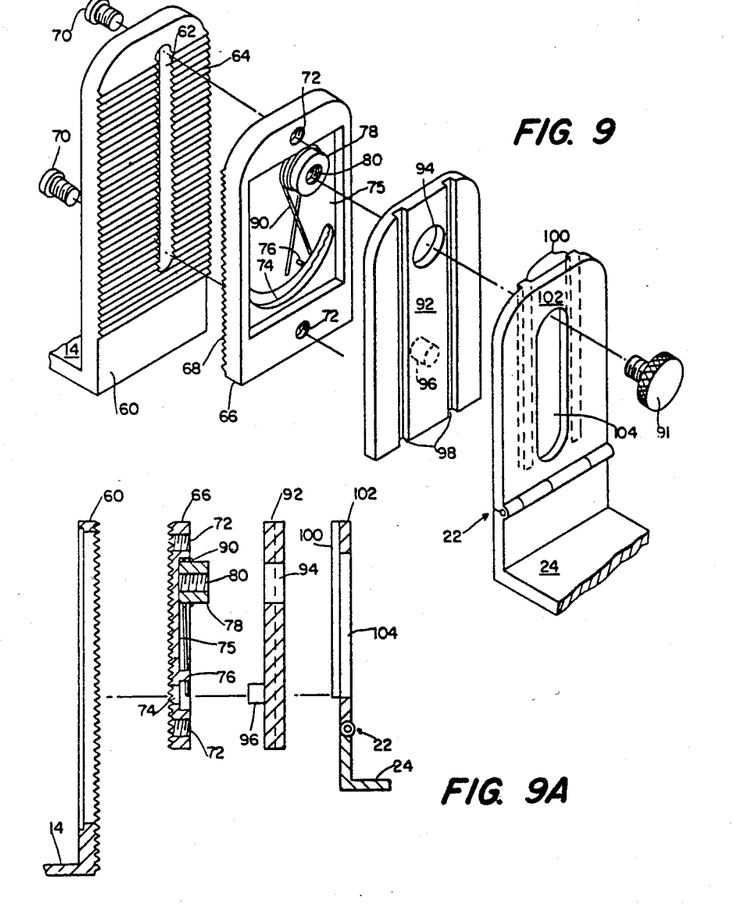
FIGS. 9 and 9A are an expanded perspective view and a side view, respectively, showing another embodiment of a link positioning means.

Another embodiment of plate pivot means 10, which additionally provides a means to allow hinge element 22 to slide vertically with respect to upstanding plate 60, is depicted in FIGS. 9 and 9A. Like the previous embodiment of plate pivot means 10, this embodiment includes an upstanding plate 60 and a facing plate 66 which are relatively adjustable as previously described. Mounted on pivot post 78 of facing plate 66 is spiral spring 90 whose crossed ends lie on either side of peg 76. Also mounted rotatably on pivot post 78 by a bore 94 is a pivot arm 92. Pivot arm 92 includes a raised key 96 on one face which extends into arcuate keyway 74 in facing plate 66. On the other face of pivot arm 92, two vertical channels 98 are positioned on either side of bore 94. Two mating raised ridges 100 on a sliding plate 102 ride in vertical channels 98. Sliding plate 102 includes a vertical slot 104 through which the end of pivot post 78 protrudes slightly. Hinge element 22 is attached at the lower end of sliding plate 102. A screw 90, passing through bore 94 and vertical slot 104 into threaded bore 80 of pivot post 78, holds pivot arm 92 and sliding plate 102 on facing plate 66.

In operation, this embodiment functions much like the embodiment discussed previously. Facing plate 66 is vertically adjustable relative to upstanding plate 60 and the angular pivoting of pivot arm 92 is both restricted and urged perpendicular. Unlike the previous embodiment, however, hinge element 22 can slide vertically with respect to pivot arm 92 and hence upstanding plate 60. When a vertical force is exerted on hinge element 22, sliding plate 102 moves freely along pivot arm 92 guided by raised ridges 100 sliding in vertical channels 98. The vertical movement of sliding plate 102 is limited by the end of vertical slot 104 in which pivot post 78 extends.

While the present invention has been described with adjusting devices which are adjusted about horizontal axes perpendicular or parallel (or both) to the longitudinal axis of the shoe, it is also specifically envisioned that the adjustment devices can operate about horizontal axes which are oblique to the perpendicular or parallel axes of the shoe. An adjustment device 200 of this nature is depicted in FIGS. 10 to 12.

Adjustment device 200 includes a heel plate 202 and a toe plate 204. As shown best in FIG. 10, heel plate 202 abuts toe plate 204 along a vertical plane represented by line 206. Line 206 forms an angle with longitudinal axis 207 of between 10° and 80°, and is preferably about 53°.

Figures 10, 11, 12:
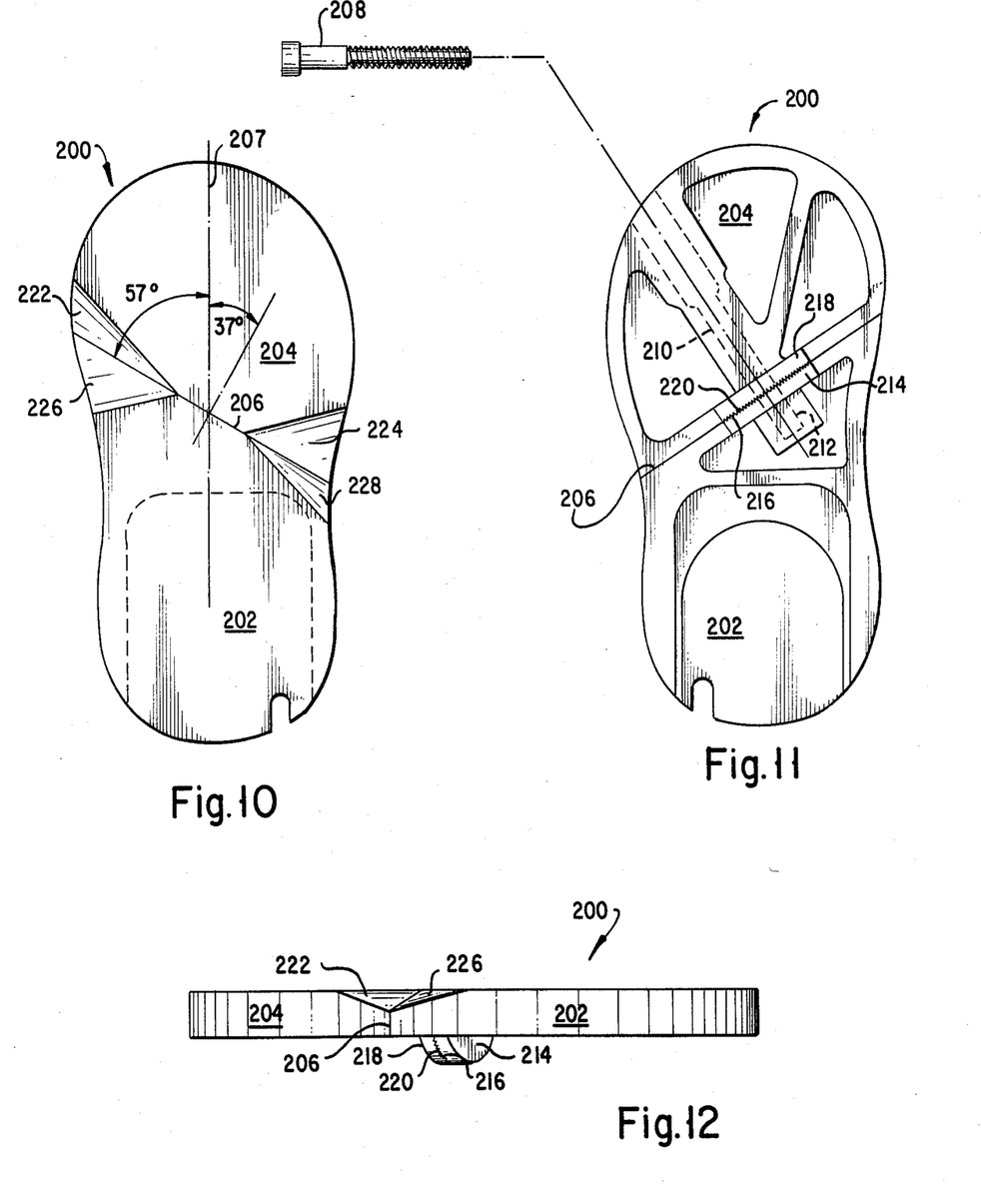
FIG. 10 is a top plan view of an alternative embodiment of adjusting mechanism for the toe of a shoe.
FIG. 11 is a bottom plan view of the adjusting mechanism for the toe of the shoe depicted in FIG. 10
FIG. 12 is a left side view of the adjusting mechanism for the toe of the shoe depicted in FIG. 10.

Toe plate 204 is joined to heel plate 202 by a screw 208 as shown in FIG. 11. Screw 208 is received in a counter-sunk bore 210 which extends at right angles to line 206. The end of screw 208 is received in a threaded bore 212 located in heel plate 202. Thus, when screw 208 is not tightened in threaded bore 212, toe plate 204 is free to rotate about the axis of screw 208 relative to heel plate 202.

Depending from heel plate 202 is a heel flange 214. Heel flange 214 is semi-circular shaped and includes a serrated face 216 parallel to line 206. The center of semi-circularly shaped heel flange 214 is coaxial with the axis of screw 208. Toe plate 204 similarly includes a toe flange 218 which depends from toe plate 204 opposite heel flange 214. Toe flange 218 is shaped similarly to heel flange 214 and includes a serrated face 220 which mates with serrated face 216 when screw 208 is tightened in threaded bore 212. Serrated faces 216 and 220 are used to securely lock toe plate 204 to heel plate 202 in a desired angular orientation when screw 208 is tightened in threaded bore 212.

When toe plate 204 is rotated relative to heel plate 202 about screw 208, one side of toe plate 204 is raised above heel plate 202 while the other side is lowered below toe plate 202. In order not to present a sharp edge of toe plate 204 to the foot on the raised portion, the outer ends of toe plate 204 along line 206 have angled portions 222 and 224. Similarly, heel plate 202 also includes angled portions 226 and 228.

In operation, adjustment device 200 functions in the following manner. It should be appreciated that adjustment device 200 is used in place of the other adjustment devices described above in order to preserve or control the mid-tarsal joint of the foot of the user. Where the other adjustment devices described above are used, an external rotation is imposed on the foot of the user and a flat foot may be inadvertently created. The pressure of this rotation is against the mid-tarsal joint alone and the forefoot/rearfoot angle is not maintained. With adjustment device 200, the mid-tarsal joint is preserved, maintained, and protected. Inversion and dorsiflexion is needed at the same time to maintain the mid-tarsal joint and to correct the deformity.

In order to adjust toe plate 204 relative to heel plate 202, screw 208 is loosened in threaded bore 212 a sufficient distance to allow serrated face 216 to clear serrated face 220. At this time, toe plate 204 is easily angularly adjusted about screw 208 relative to heel plate 202. When the desired angular orientation is achieved, screw 208 is again advanced in threaded bore 212 to bring serrated face 216 into contact with serrated face 220. This locks toe plate 204 at the desired angular orientation relative to heel plate 202. It should be appreciated that angled portions 222, 224, 226, and 228 are provided so that a sharp angle between toe plate 204 and heel plate 202 at the sides is not presented to the foot of the user (located in attached shoes 13, not shown).

By use of shoes 13, a number of deformations of the foot of a patient are treatable, including forefoot adductions, hind foot inversions and hind foot equinus. In addition, if the patient also requires a foot splint, shoes 13 are readily usable with such a device as well. While shoes 13 have been shown in use with a specific foot splint, other foot splint designs are also usable with shoes 13 as desired. The specific adjustment mechanisms used to adjust the toe portion relative to the heel portion can also be varied. Thus, although the present invention has been described with respect to exemplary embodiments thereof, it will be understood by those of ordinary skill in the art that variations and modifications may be affected within the scope and spirit of the invention.

What is claimed:

1. An orthopedic appliance comprising:
an orthopedic shoe having a longitudinal and axis and a lateral axis which are in a horizontal plane, said shoe being separated into a heel portion and a toe portion;
a heel plate to said heel portion is attached;
a toe plate to which said toe portion is attached;
adjusting means for adjusting the plane of said toe plate relative to the plane of said heel plate about a horizontal axis disposed at an angle only within the range, of 10° to 80° with respect to the longitudinal axis of said shoe; and
locking means for locking said toe plate relative to said heel plate in the adjusted position.

2. An orthopedic appliance as claimed in claim 1 wherein said toe plate is adjusted about an axis disposed at about 37° to the longitudinal axis of said shoe.

3. An orthopedic appliance as claimed in claim 1 and further including angled portions adjacent the lateral sides of said toe plate and said heal plate whereby the top portions of said plates adjacent the lateral sides are cut away to present a smoother boundary between said toe plate and said heel plate when said plates are angularly adjusted relative to one another.

4. An orthopedic appliance as claimed in claim 3 wherein said angled portions are triangularly shaped.

5. An orthopedic appliance as claimed in claim 1 wherein said locking means including a toe flange depending from the bottom of said heel plate and a heel flange depending from the bottom of said heel plate and adajacent to said toe flange such that said flanges are locked together after adjustment of said toe plate relative to said heel plate.

6. An orthopedic appliance as claimed in claim 5 wherein said flanges are rounded on the bottom and provide a ground contacting surface for said shoe.

7. An orthopedic appliance as claimed in claim 1 and further including attaching means mounted on said heel plate for attaching said shoe to an orthopedic foot splint.

8. An orthopedic appliance as claimed in claim 7 wherein a pair of said shoes are attached to said orthopedic foot splint and said orthopedic foot splint includes means for preventing any relative rotation about a vertical axis between said shoes with respect to each other while permitting freedom of movement of said shoes about axes other than the vertical axis.

9. An orthopedic appliance as claimed in claim 8 wherein said foot splint further includes a means for adjusting the longitudinal axes of said heel portions of said pair of shoes in a selected angular relationship with respect to each other.

* * * * *